(12) United States Patent
Falkenberg

(10) Patent No.: US 7,195,628 B2
(45) Date of Patent: Mar. 27, 2007

(54) ATRIAL FIBRILLATION THERAPY WITH PULMONARY VEIN SUPPORT

(75) Inventor: Eric Falkenberg, Simi Valley, CA (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 554 days.

(21) Appl. No.: 10/316,488

(22) Filed: Dec. 11, 2002

(65) Prior Publication Data

US 2004/0116965 A1   Jun. 17, 2004

(51) Int. Cl.
*A61B 18/18* (2006.01)

(52) U.S. Cl. ............... 606/41; 623/1.42; 623/1.46; 604/20

(58) Field of Classification Search ............ 607/2, 607/5–8; 606/41; 604/509, 20; 623/1.11–1.12, 623/1.15, 1.18, 900, 1.42, 1.46
See application file for complete search history.

(56) References Cited

U.S. PATENT DOCUMENTS

| | | | |
|---|---|---|---|
| 5,078,736 A | | 1/1992 | Behl ........................ 623/1 |
| 5,497,774 A | | 3/1996 | Swartz et al. ............. 128/658 |
| 5,531,779 A | | 7/1996 | Dahl et al. ................ 607/119 |
| 5,575,766 A | | 11/1996 | Swartz et al. ............ 604/53 |
| 5,715,818 A | | 2/1998 | Swartz et al. ............ 128/642 |
| 5,725,512 A | | 3/1998 | Swartz et al. ............ 604/280 |
| 5,749,914 A | * | 5/1998 | Janssen ...................... 607/116 |
| 6,012,457 A | * | 1/2000 | Lesh ........................... 128/898 |
| 6,064,902 A | * | 5/2000 | Haissaguerre et al. ....... 600/381 |
| 6,117,101 A | | 9/2000 | Diederich et al. ............ 604/22 |
| 6,251,109 B1 | | 6/2001 | Hassett et al. ............... 606/45 |
| 6,258,121 B1 | * | 7/2001 | Yang et al. ................ 623/1.46 |
| 6,632,223 B1 | * | 10/2003 | Keane ........................ 606/41 |
| 6,716,242 B1 | * | 4/2004 | Altman ...................... 623/1.42 |
| 6,949,113 B2 | * | 9/2005 | Van Tassel et al. ......... 606/200 |
| 2001/0004705 A1 | | 6/2001 | Killion et al. |
| 2001/0032014 A1 | | 10/2001 | Yang et al. |
| 2001/0035456 A1 | | 11/2001 | Lennox |
| 2002/0002349 A1 | | 1/2002 | Flaherty |
| 2002/0010461 A1 | | 1/2002 | KenKnight et al. |
| 2002/0013275 A1 | | 1/2002 | Kunz |
| 2002/0183682 A1 | * | 12/2002 | Darvish et al. ............... 604/20 |

* cited by examiner

*Primary Examiner*—Robert Pezzuto
*Assistant Examiner*—Shevon Johnson
(74) *Attorney, Agent, or Firm*—Wiley Rein LLP

(57) ABSTRACT

A system and method for treatment of paroxysmal atrial fibrillation by destruction of conductive pathways between the pulmonary veins and the left atrium. A stent is delivered by catheter to the left atrium and to the ostium of a pulmonary vein to be treated. The stent is positioned in the pulmonary vein and is deployed to engage and support the pulmonary vein. The stent prevents stenosis of the pulmonary vein as a result of ablation of tissue. The ablation is produced by a coating of a biologically active material on the stent which destroys tissue or slows electrophyisiologic conduction through the tissue. Alternatively, ablation is performed using RF energy, cryoablation, laser energy, or other ablation techniques.

16 Claims, 3 Drawing Sheets

ATRIAL FIBRILLATION THERAPY WITH PULMONARY VEIN SUPPORT

CROSS-REFERENCE TO RELATED APPLICATION(S)

None.

BACKGROUND OF THE INVENTION

The present invention is a device and method of treating atrial fibrillation by selective ablation of tissue to treat focal arrhythmia arising from and about a pulmonary vein, and by support of the pulmonary vein against stenosis subsequent to ablation.

The human heart has four chambers. The two upper chambers are the left and right atrium, and the two lower chambers are the left and right ventricles. Blood from the veins of the body returns to the right atrium of the heart. When the right atrium contracts, the blood passes from the right atrium through the tricuspid valve to the right ventricle. The blood is then pumped by contraction of the right ventricle through the pulmonary artery to the lungs. In the lungs, carbon dioxide passes out of the blood, and oxygen passes into the blood. The oxygenated blood returns from the lungs through the pulmonary veins to the left atrium. The blood is pumped by contraction of the left atrium through the mitral valve to the left ventricle. Contraction of the left ventricle pumps the blood out of the left ventricle to the aorta and through the arteries to the body.

The normal beating of the heart is the result of a coordinated set of muscle contractions and relaxations. The normal resting heart rate is about 60 to 80 beats per minute. The coordinated contractions and relaxations are referred to as sinus rhythm.

The contraction of heart muscle occurs in response to electrical impulses which trigger fibers of heart muscle to contract in a coordinated fashion. During sinus rhythm, the heart beat starts in the right atrium with an electrical impulse at the sinoatrial (SA) node. The impulse spreads through the right and left atrium and then to the atrio-ventricular (AV) node. The AV node is an electrical pathway that transmits electrical signals from the atria to the ventricles. The electrical signal travels from the AV node along a common pathway and then splits into left and right bundle branches to activate the left and right ventricles. The sequence of activation results in efficient pumping. The atria contract first, and pump blood to the ventricles. The ventricles then contract and pump blood to the lungs and the body. During sinus rhythm, the AV node permits the ventricles to beat at the same rate as the atrium, but with a slight delay which allows the atria to empty their blood into the ventricles before the ventricles contract.

In atrial fibrillation, the electrical signals that normally coordinate the regular contractions of muscle fibers in the atrium are disorganized, resulting in rapid and disorganized contraction of individual muscle fibers. The atria quiver instead of beating effectively. During atrial fibrillation, the atrial muscle activates at rates that can exceed 300 beats per minute. The atria no longer pump blood efficiently to fill the ventricles. This can result in a variety of chronic and undesirable conditions. Atrial fibrillation can increase the rate of stroke, congestive heart failure and cardiomyopathy. It can also damage normal heart muscle or change the nature of electrical conduction and the patterns of contraction and relaxation of the heart muscle.

Atrial fibrillation is the most common sustained heart arrhythmia. It is estimated to occur in upwards of 0.4 percent of the adult population and perhaps as many as 10 percent of the population who are 60 years or older. Cox, J. L., et al., Electrophysiology, Pacing and Arrhythmia, "Operations for Atrial Fibrillation," Clin. Cardiol. 14, 827–834 (1991).

Atrial fibrillation can be paroxysmal, persistent or chronic. Paroxysmal atrial fibrillation occurs from time to time. It may vary in duration from a few seconds to several hours, and may vary in intensity and is self terminating. Persistent atrial fibrillation occurs from time to time and requires a clinical intervention to terminate. Chronic atrial fibrillation is one in which clinical interventions are not successful or yield a termination that is of a short duration that is not deemed clinically significant.

During atrial fibrillation, blood flow in some parts of the left atrium can stagnate. This can trigger the formation of blood clots within the left atrium, and if these blood clots subsequently pass from the left atrium to the left ventricle, they may be pumped into the general circulation of the body. If a clot lodges in an artery in the brain, the result is a stroke. Approximately 25% of all strokes are related to atrial fibrillation, with up to 70% of those resulting in death or significant neurological deficit.

Several treatments have been developed for atrial fibrillation which include pharmacological approaches, surgical approaches, and catheter-based ablation techniques. Antiarrhythmic drugs have not proven to be very effective, with trial data showing up to 60% of patients not sustaining a normal heart rhythm for one year. In addition, there is an increased risk of developing a life-threatening ventricular arrhythmia.

Other treatments for atrial arrhythmia or fibrillation involve the use of an implanted atrial defibrillator or cardioversion. See, for example, U.S. Pat. Nos. 5,282,836, 5,271,392 and 5,209,229 and Martin, D., et al., Atrial Fibrillation, pages 42–59 (1994). Initial conversion from atrial fibrillation to normal heart rhythm is high; however, reversion rates are also high. Additionally, patient discomfort levels are often unacceptable.

Certain patients with symptomatic or life threatening atrial arrhythmia, however, cannot be adequately treated by drugs or these types of medical devices. Other forms of aggressive treatment are sometimes mandated, which have in the past included surgery. For example, a surgical procedure for the treatment of atrial arrhythmia known as the "Maze" procedure is discussed in Cox, J. L. et al., Electrophysiology, Pacing and Arrhythmia, "Operations for Atrial Fibrillation," Clin. Cardiol. Vol. 14, pages 827–834 (1991). However, this procedure requires open-heart surgery, which is very risky to the patient.

Another procedure increasingly used within the last 10 to 15 years for the treatment of certain types of cardiac arrhythmia involves ablation of cardiac tissue. For example, this procedure has been commonly used to interrupt or modify existing conduction pathways associated with arrhythmia within the heart. The particular area for ablation depends on the type of underlying arrhythmia. The use of radio frequency catheter ablation for the treatment of paroxysmal atrial fibrillation is disclosed in Haissaguerre, M., et al., "Right and Left Atrial Radiofrequency Catheter Therapy of Paroxysmal Atrial Fibrillation" J . Cardiovascular Electrophysiology, V. 7, pages 1132–1144 (December 1996). Ablation procedures have also been used for the treatment of atrioventricular (AV) nodal reentrant tachycardia. With this condition, ablation of the fast or slow AV nodal pathways has become an accepted treatment. Singer, I., et al., "Catheter Ablation for Arrhythmias" Clinical Manual of Electrophysiology, pages 421–431 (1993); Falk, R. H., et al., Atrial Fibrillation Mechanisms in Management, pages 359–374 (1992); Horowitz, L. N., Current Management of Arrhythmias, pages 373–378 (1991); and Martin, D., e addition, the use of ablation catheters for ablating locations within the heart has been disclosed, for example, in U.S. Pat. Nos. 4,641,649, 5,263,493, 5,231,995, 5,228,442 and 5,281,217.

The sources of energy used for catheter ablation vary. Initially, high voltage, direct current (DC) ablation techniques were commonly used. However, because of problems associated with the use of DC current, radio frequency (RF) energy has become the preferred source of energy for ablation procedures. The use of RF energy for ablation has been disclosed, for example, in U.S. Pat. Nos. 4,945,912, 5,209,229, 5,281,218, 5,242,441, 5,246,438, 5,281,213 and 5,293,868. Other energy sources which are being used currently or are being considered for ablation of heart tissue include laser, ultrasound, and microwave.

Ablation of a precise location within the heart requires the precise placement of the ablation catheter within the heart. Precise positioning of the ablation catheter is especially difficult because of the physiology of the heart, particularly as the ablation procedures generally occur while the heart is beating. Commonly, the placement of the catheter is determined by a combination of electrophysiological guidance and fluoroscopy (placement of the catheter in relation to known features of the heart which are marked by radiopaque diagnostic catheters that are placed in or at known anatomical structures such as the coronary sinus, high right atrium and the right ventricle).

A process for the mapping and treatment of atrial arrhythmia using ablation catheters guided to a specific location by shaped, guiding introducers is disclosed in U.S. Pat. Nos. 5,427,119, 5,497,774, 5,575,766, 5,564,440, 5,628,316 and 5,640,955. In particular, a process for the ablation of defined tracks within the left and/or right atrium as an element of the treatment of atrial fibrillation is disclosed in U.S. Pat. No. 5,575,766.

The mechanism for initiation of some forms of atrial arrhythmia, such as atrial premature contractions, is not well understood. As a result, ablation procedures in the heart have focused on the formation of lesions within the chambers of the heart at selected locations which either prevent the passage of electrical signals associated with atrial premature contractions or prevent the formation of improper electrical pathways within the heart, which can result in atrial arrhythmia.

It has been discovered that one source for these atrial premature contractions originates within vessels associated with the heart, in particular the pulmonary veins. Once these atrial premature contractions form in the pulmonary veins, they are periodically conducted into the left atrium. When the atrial premature contractions enter the left atrium, they can initiate or continue an episode of atrial fibrillation.

Invasive treatment of atrial fibrillation in the past around the pulmonary veins has been directed to the formation of lesions in the left atrium created by an invasive surgical procedure, such as is disclosed by Cox, J. L., et al., Electrophysiology, Pacing and Arrhythmia, "Operations for Atrial Fibrillation" Clin. Cardiol. Volume 14, pages 827–834 (1991). In addition, the use of precurved guiding introducers to guide ablation catheters to appropriate locations in the left atrium for use in the formation of lesions around the pulmonary veins has been disclosed in U.S. Pat. No. 5,575,766.

Catheter-based ablation techniques used to target the focal arrhythmias in the pulmonary veins are described in U.S. Pat. Nos. 6,251,109 and 6,117,101. These techniques either destroy the tissue which is producing the unwanted electrical activation or destroy conductive pathways to electrically isolate the pulmonary vein from the left atrium. This is typically accomplished by positioning the distal tip of a guide catheter within the left atrium. A typical approach is a transeptal approach in which guide catheter is introduced into a peripheral vein (such as a femoral vein) and is advanced along the peripheral vein, into the vena cavae and into the right atrium. The distal tip of the guide catheter is positioned against the fossa ovalis of the atrial septum which divides the left and right atrium. An access port is created through the septum, and the distal tip of the guide catheter is advanced across the septum and into the left atrium. Alternatively, access to the left atrium can be achieved by advancing the guide catheter through the arterial system to the left ventricle and through the mitral valve to the left atrium.

Using a guiding introducer or other device, the ostium of a pulmonary vein is located. Mapping devices may be used to perform electrical mapping of the conduction potentials in the pulmonary veins. The tissue around the ostia and inside the ostia is selectively or grossly targeted for destruction in an attempt to interrupt conduction pathways thought to be the source of paroxysmal, persistent or chronic atrial fibrillation initiation.

DC current, RF energy, laser energy, microwave energy, ultrasound or cryoablation is used to ablate the desired region of tissue. Sometimes a partial or complete circumferential path is defined to provide a block which electrically isolates the pulmonary vein from the left atrium. Catheter ablation treatment for atrial fibrillation can result in complications. One negative outcome of ablation is the reaction that leads to a stenosis or narrowing of the treated pulmonary vein. This stenosis, if of a significant degree, can lead to a potentially morbid or mortal result as a consequence of induced pulmonary hypertension.

BRIEF SUMMARY OF THE INVENTION

The present invention is a device and method of treating atrial fibrillation in which tissue in or near a pulmonary vein is ablated to treat focal arrhythmia arising from the pulmonary vein. In order to prevent stenosis in the pulmonary vein resulting from the ablation of tissue, a stent is deployed within the pulmonary vein.

The stent may be deployed following ablation of tissue by an ablation catheter. Alternatively, the stent may produce the ablation by delivering a biologically active agent which either destroys pulmonary vein tissue or inhibits its electrophysiologic conduction properties.

DETAILED DESCRIPTION

Figure 1:
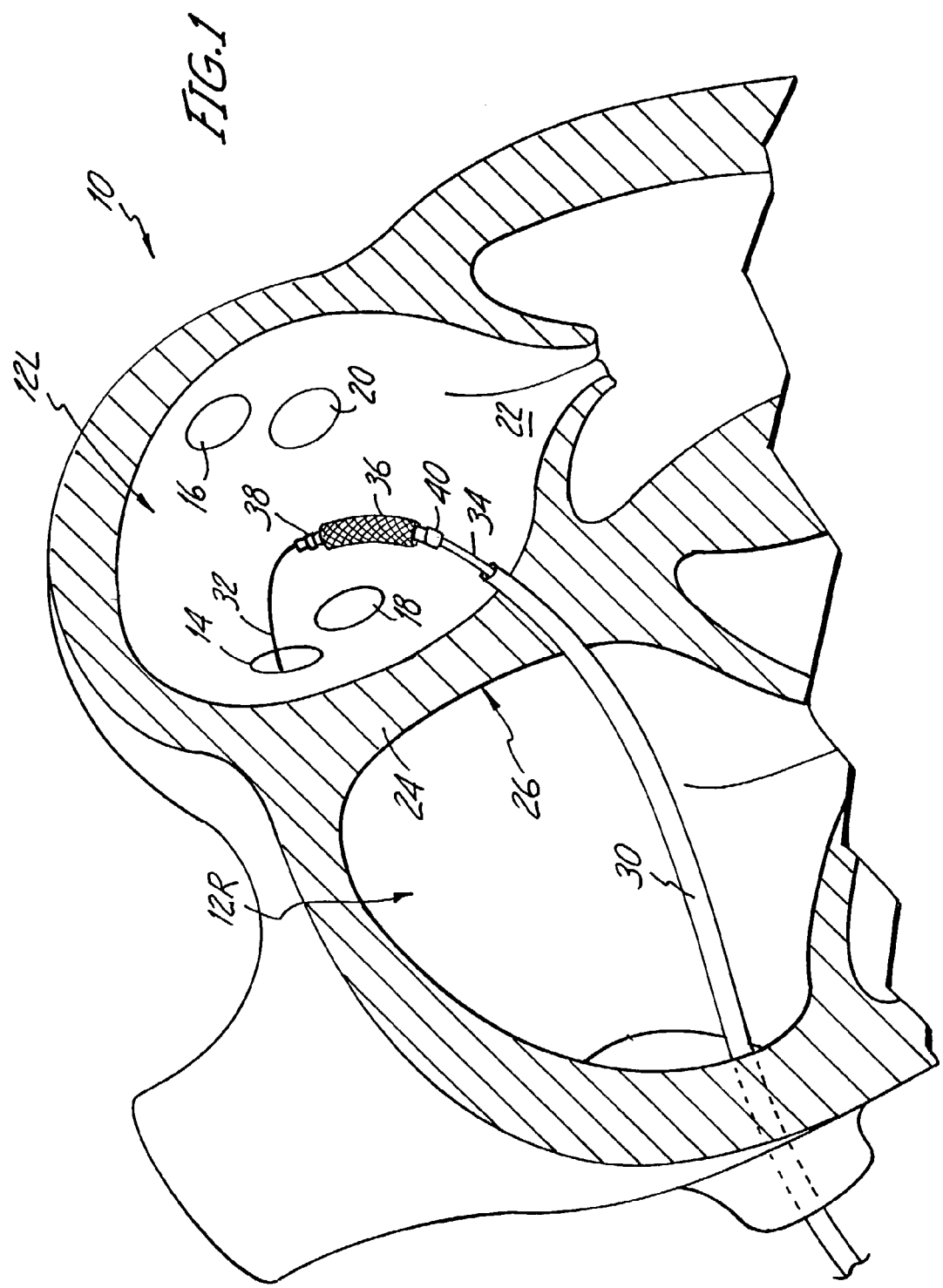
FIG. 1 is a schematic drawing of the left atrium showing a stent delivery catheter being advanced on a guidewire from a distal end of a guide catheter to a pulmonary vein.

The human heart includes two upper chambers called the left atrium and right atrium, and two lower chambers called the left ventricle and right ventricle. FIG. 1 shows a sectional schematic view of a portion of heart 10 in which a catheter based ablation treatment is being performed to treat atrial fibrillation. Shown in FIG. 1 are left atrium 12, right superior pulmonary vein 14, left superior pulmonary vein 16, right inferior pulmonary vein 18, and left inferior pulmonary vein 20. Also shown in FIG. 1 are mitral valve 22, atrial septum 24, and fossa ovalis 26.

The present invention is a catheter-based ablation therapy in which conductive pathways in pulmonary veins 14, 16, 18, and 20 are destroyed in order to electrically isolate sources of unwanted electrical impulses (arrhythmiatic foci) located in the pulmonary veins. By either destroying the arrhythmiatic foci, or electrically isolating them from the left atrium, the initiation of paroxysmal atrial fibrillation can be reduced or eliminated.

The present invention makes use of a catheter delivered expandable support device (or stent) to maintain patency of the pulmonary vein following ablation therapy. Preferably, the ablation therapy is also delivered in the same process.

As shown in FIG. 1, the present invention includes guide catheter 30, guide wire 32, stent delivery catheter 34, stent 36, and mapping electrodes 38 and 40. In operation, guide catheter 30 has its distal end positioned within left atrium 12L. FIG. 1 illustrates a transeptal approach in which guide catheter 30 has been introduced through a peripheral vein (typically a femoral vein) and advanced to right atrium 12R. An opening has been provided in fossa ovalis 26 which allows distal end of guide catheter 30 to enter left atrium 12L.

Guide catheter 30 can also be introduced into left atrium 12L through the arterial system. In that case, guide catheter 30 is introduced into an artery (such as a femoral artery) and advanced retrograde through the artery to the aorta, the aortic arch, and into the left ventricle. Guide catheter 30 enters left atrium 12L through mitral valve 22.

Once guide catheter 30 is in position within the left atrium 12L, guide wire 32 and stent delivery catheter 34 are advanced out the distal end of guide catheter 30 and toward one of the pulmonary veins. In FIG. 1, the target pulmonary vein is right superior pulmonary vein 14. Guide wire 32 is shown having entered the ostium of pulmonary vein 14.

Stent delivery catheter 34 may be either an over-the-wire or a fixed-wire catheter. If it is an over-the-wire catheter, then guide wire 32 is first advanced into pulmonary vein 14, and stent delivery catheter 34 is then advanced over guide wire 32. In a fixed-wire configuration, guide wire 32 is attached to and extends out the distal end of stent delivery catheter 34, so that guide wire 32 and catheter 34 move together as guide wire 32 locates and then enters pulmonary vein 14.

Carried near the distal end of catheter 34 is stent 36. As seen in FIG. 1, stent 36 is in its collapsed condition so that it can pass through guide catheter 30, and can enter pulmonary vein 14. Stent 36 is expandable when deployed, so that it engages and supports the interior wall of pulmonary vein 14 and its ostium.

Also shown in FIG. 1 are mapping electrodes 38 and 40. Mapping electrodes 38 and 40 are ring electrodes that allow the clinician to perform a pre-deployment electrical mapping of the conduction potentials of the pulmonary vein. Although shown as being carried on stent delivery catheter 34, mapping electrodes 38 and 40 can alternatively be carried on stent 36.

Stent 36 is preferably coated with a biologically active material that is a cytocidal agent or that has an ability to slow or block electrophysiologic conduction. Cytocidal agents that may be used include, but are not limited to, agents such as TGF-β production or activation stimulators such as tomoixifen or TGF-β, Taxol or analogs thereof, Riridin A and *Pseudomonas* exotoxin or analogs thereof, and protein kinase inhibitors. These and other candidate therapeutic agents are described in U.S. Pub. No. 2002/0013275 A1, published Jan. 31, 2002 for "Therapeutic Inhibitor of Vascular Smooth Muscle Cells" by L. Kunz, et al. In this embodiment, stent 36 is used both to deliver the ablation therapy and also to support the pulmonary vein 14 after ablation to maintain patency of the pulmonary vein 14 and prevent stenosis.

In an alternative embodiment, a cytostatic agent also coats stent 36 to prevent stenosis. The cytostatic agent is delivered at a dose and for a duration such that cell proliferation, contraction, or migration is inhibited during a period when stenosis would occur. Examples of such agents include protein kinase inhibitors, TGF-β production or activation stimulators such as tamoxifen or TGF-β, Taxol and its analogs, smooth muscle contraction and/or migration inhibitors such as the cytochalasins, surmin, and nitric oxide-releasing compounds. These and other candidate therapeutic agents are described in U.S. Pub. No. 2002/0013275 A1, published Jan. 31, 2002 for "Therapeutic Inhibitor of Vascular Smooth Muscle Cells" by L. Kunz, et al. Thus, the combination of stent 36 and the cytostatic agent greatly reduce the occurrence of stenosis after ablation therapy.

A method of coating stent 36 with therapeutic agents is described in U.S. Pub. No. 2001/0032014 A1, published Oct. 18, 2001, for "Stent Coating" by Y. Daikon, et al. The therapeutic agents are embedded in a substrate that may or may not be biodegradable and covers stent 36. In the present invention, the cytocidal agent is embedded in a substrate that quickly releases a toxic dose of cytocidal agent to the tissue. The cytostatic agent is embedded in a second substrate that slowly releases a nontoxic dose of the cytostatic agent to the same area. The cytocidal agent and the cytostatic agent may be the same therapeutic agent delivered at different doses and on different substrates, or they may be different agents.

Alternatively, if stent 36 is electrically conductive (e.g., metal), stent 36 may deliver DC current energy to ablate the tissue of the pulmonary vein. Stent 36 may also be utilized as an antenna to receive RF energy to ablate the tissue. Stent 36 may or may not be coated with the cytostatic agent but remains in position to maintain patency of the pulmonary vein.

In yet another embodiment, if stent 36 is electrically conductive, stent 36 may be used for electroporation or iontophoresis. Stent 36 may apply heat or short pulses of high electric fields to the engaged tissue, which cause the cell membranes to become porous, allowing the therapeutic agents to more readily diffuse into the cells. Alternatively, if a polar therapeutic agent is used, or if the agent is made polar through conjugation to a polar moiety, stent 36 may apply a current which promotes delivery of the agent to the tissue.

These delivery methods are more practical for delivering the cytocidal agents which immediately act upon the target tissue.

Figure 2:
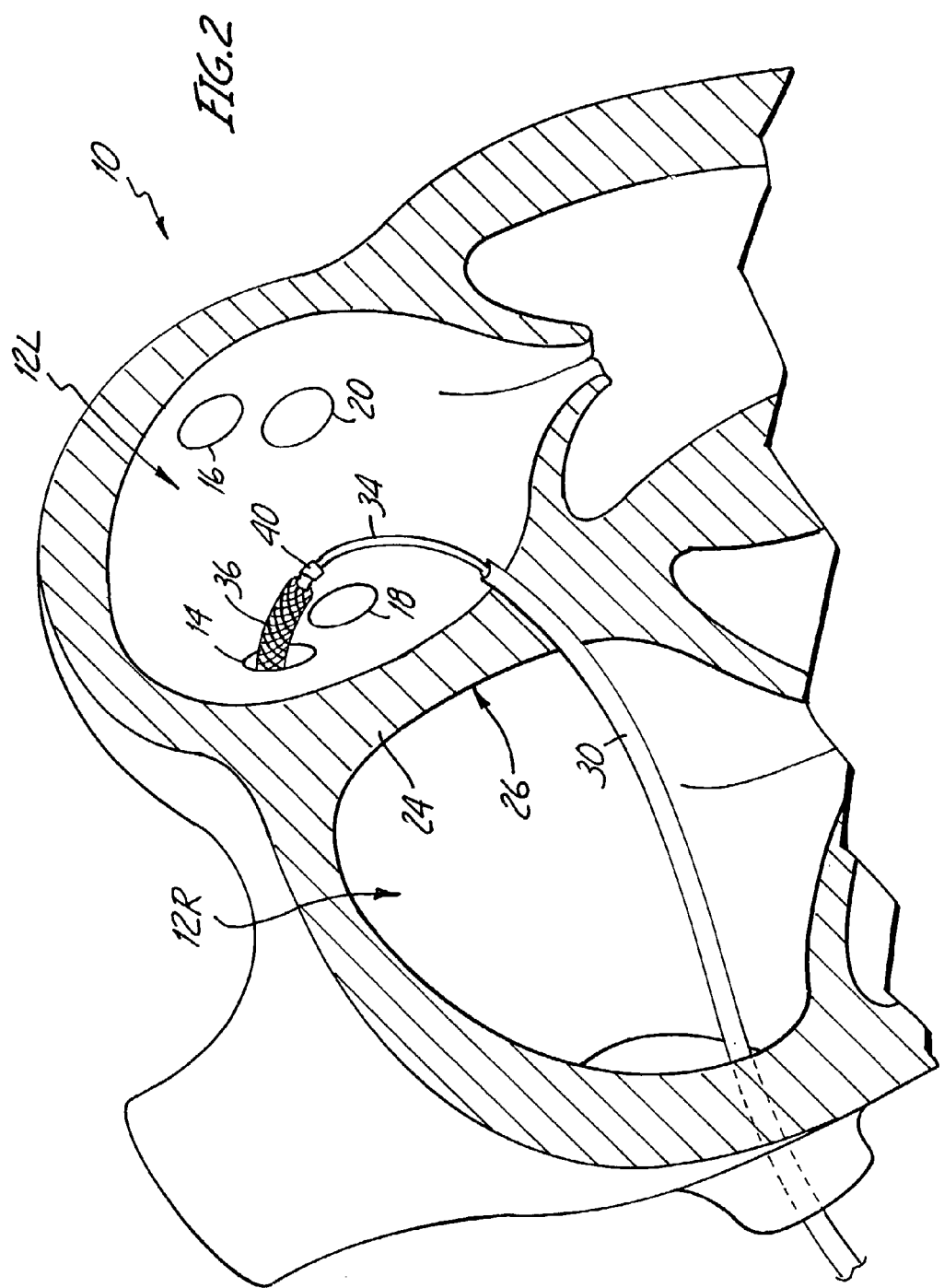
FIG. 2 is a schematic diagram of the left atrium showing the stent delivery catheter being advanced into the pulmonary vein.

FIG. 2 is similar to FIG. 1 and shows stent delivery catheter 34 as it has advanced further and stent 36 has entered the ostium of pulmonary vein 14. As catheter 34 enters pulmonary vein 14, mapping will be performed using electrodes 38 and 40 in order to select the proper location for deployment of catheter 36.

Figure 3:
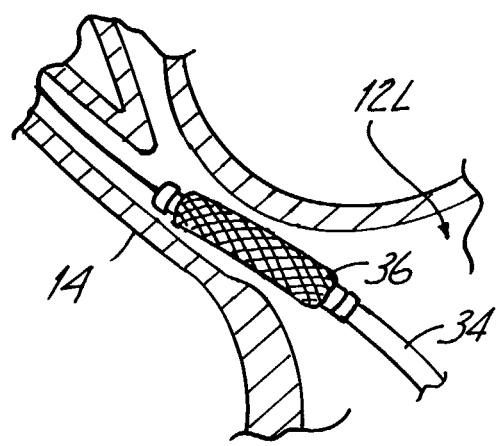
FIG. 3 is a sectional view of the pulmonary vein showing the stent delivery catheter and the stent in position within the pulmonary vein prior to deployment of the stent.

FIG. 3 shows catheter 34 with stent 36 now in position prior to deployment. The proper location of stent 36 has been determined by mapping. As shown in FIG. 3, stent 36 is still in its collapsed condition.

Figure 4:
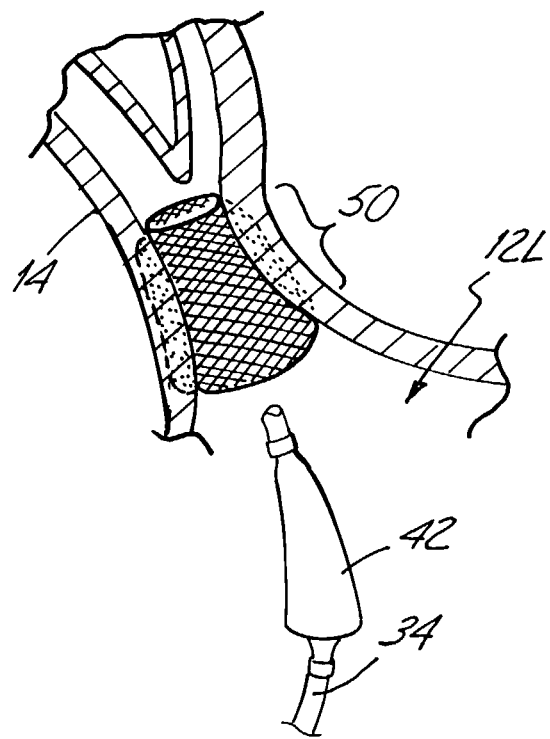
FIG. 4 is a sectional view of the pulmonary vein showing the deployed stent in its expanded condition after the stent delivery catheter has been withdrawn from the pulmonary vein.

FIG. 4 shows stent 36 after it has expanded radially to its expanded or erected state. Stent 36 has a tapered shape with the distal end having a diameter that is smaller than the diameter at the proximal end. This is the preferred shape to support the ostium of pulmonary vein 14. The tapered shape may be achieved by forming stent 36 over a tapered tool using a shape memory metal such as nitinol. This method of production creates self-expanding stents. Other suitable materials may also be used to create stent 36 and then two different internal radial forces are used to expand stent 36. For example, a first smaller balloon expands the distal end and a second larger balloon expands the proximal end. Stents possessing these qualities are described in more detail in U.S. Publ. No. 2002/0004705 A1, published Jun. 21, 2002, for "Stent Having Variable Properties and Method of Its Use" by D. Killiom, et al.

As illustrated in FIG. 4, catheter 34 has an expandable balloon 42 which was located under stent 36, and which was expanded in order to radially expand and erect stent 36. Balloon 42 represents the second balloon deployed to expand the proximal end of stent 36. Once stent 36 is in position and anchored within pulmonary vein 14, balloon 42 is collapsed so that catheter 34 disengages and leaves stent 36 in position. Once balloon 42 is collapsed, delivery catheter 34 can be withdrawn into guide catheter 30.

In its expanded or erected state shown in FIG. 4, stent 36 engages the inner walls of pulmonary vein 14, to prevent the walls from collapse. In addition, the erection of stent 36 has brought the coated surface of stent 36 into contact with the tissue on the inner walls of pulmonary vein 14. The biologically active coating on the outer surface of stent 36 contacts the inner wall of pulmonary vein 14 and its ostium to produce a circumferential zone of ablation 50. Ablation zone 50 electrically isolates pulmonary vein 14 from left atrium 12L. To the extent that arrhythmiatic foci were located within ablation zone 50, they are destroyed. To the extent the arrhythmiatic foci are located in pulmonary vein 14 on the opposite side of ablation zone 50 from left atrium 12L, the electrical impulses produced by those foci are blocked or inhibited by ablation zone 50. Stent 36, with or without the cytostatic agent, prevents stenosis from occurring.

In a typical treatment, pulmonary veins are treated in accordance to their likelihood of having an arrhythmiatic focus. Often, all pulmonary veins are treated. The processes as described for right superior pulmonary vein 14 is similar for each of the three other pulmonary veins 16, 18, and 20.

The use of a biologically active material carried by stent 36 to produce an ablation effect offers an advantage over other ablation techniques which are dependent upon heat (such as RF energy, DC current, ultrasound or laser ablation techniques). There is a potential for formation of coagulum when using a heat based ablation technique. By destroying pulmonary vein tissue or inhibiting its physiologic conduction properties through stent delivered biologically active material, the risk of formation of coagulum that can travel through the vascular system and produce a cardiovascular accident is reduced.

The use of a catheter-delivered stent or support device through the pulmonary vein also is advantageous when other ablation techniques are used. If a circumferential ablation pattern is produced at or near the ostium of a pulmonary vein through RF energy, DC current, laser energy, ultrasound or by cryoablation, it is still important to maintain the patency of the pulmonary vein. Stenosis caused by tissue reaction to the ablation is a complication associated with those procedures. The use of a stent to maintain patency of the vein by preventing collapse of the pulmonary vein walls is an important advantage to tie present invention.

Stents have been developed for a variety of different applications and take a number of different forms. The present invention can utilize stents of various types and different mechanical construction. The stents may be either of a conductive or a nonconductive material and can be either self erecting or mechanically erected, such as through the use of a balloon as illustrated in FIG. 4.

Although the present invention has been described with reference to preferred embodiments, workers skilled in the art will recognize that changes may be made in form and detail without departing from the spirit and scope of the invention.

I claim:

1. A method of treating atrial fibrillation, the method comprising:
    accessing a left atrium with a therapeutic device;
    performing a therapy on contractile tissue in a transitional region between a pulmonary vein and the left atrium;
    deploying an expandable member to engage and support a wall of the pulmonary vein within the pulmonary vein, wherein the expandable member carries an ablation causing agent and wherein performing a therapy on contractile tissue comprises delivering the ablation causing agent via electroporation; and
    removing the therapeutic device while leaving the expandable member in engagement with the pulmonary vein to maintain patency of the pulmonary vein.

2. The method of claim 1, wherein the ablation causing agent is selected from a group consisting of cytocidal agents, cytostatic agents and combinations thereof.

3. A device for treating atrial fibrillation, the device comprising:
    a stent sized to be delivered to a left atrium through a guide catheter and expandable to engage a wall of a pulmonary vein between an arrhythmiatic focus and the left atrium; and
    a stent delivery catheter for carrying and deploying the stent;
    wherein an ablation causing agent is carried by the stent, wherein the ablation causing agent is a biologically active material, and wherein the stent utilizes electroporation to deliver the ablation causing agent to the cells of the pulmonary vein engaged by the stent.

4. The device of claim 3, wherein the ablation causing agent is selected from a group consisting of cytocidal agents, cytostatic agents and combinations thereof.

5. The device of claim 3, wherein the stent is expandable by an internal radial force.

6. The device of claim 3, wherein the stent, when expanded, is tapered such that a first end has a smaller diameter and a second end has a larger diameter.

7. A method of treating a pulmonary vein to electrically isolate arrhythmiatic foci, the method comprising:
   delivering, to an ostium of the pulmonary vein, a stent which carries at least one biologically active material; and
   deploying the stent in the pulmonary vein at a position to maintain patency of the pulmonary vein;
   wherein the biologically active material is delivered to tissue of the pulmonary vein engaged by the stent by electroporation; and
   wherein the biologically active material is an ablation causing agent.

8. The method of claim 7, wherein the stent is positioned between the arrhythmiatic foci and a left atrium.

9. A method of treating atrial fibrillation, the method comprising:
   accessing a left atrium with a therapeutic device;
   performing a therapy on contractile tissue in a transitional region between a pulmonary vein and the left atrium;
   deploying en expandable member to engage and support a wall of the pulmonary vein within the pulmonary vein, wherein the expandable member carries an ablation causing agent and wherein performing a therapy on contractile tissue comprises delivering the ablation causing agent via iontophoresis; and
   removing the therapeutic device while leaving the expandable member in engagement with the pulmonary vein to maintain patency of the pulmonary vein.

10. The method of claim 9, wherein the ablation causing agent is selected from a group consisting of cytocidal agents, cytostatic agents and combinations thereof.

11. A device for treating atrial fibrillation, the device comprising:
    a stent sized to be delivered to a left atrium through a guide catheter and expandable to engage a wall of a pulmonary vein between an arrhythmiatic focus and the left atrium; and
    a stent delivery catheter for carrying and deploying the stent;
    wherein an ablation causing agent is carried by the stent, wherein the ablation causing agent is a biologically active material, and wherein the stent utilizes iontophoresis to deliver the ablation causing agent to the cells of the pulmonary vein engaged by the stent.

12. The device of claim 11, wherein the ablation causing agent is selected from a group consisting of cytocidal agents, cytostatic agents and combinations thereof.

13. The device of claim 11, wherein the stent is expandable by an internal radial force.

14. The device of claim 11, wherein the stent, when expanded, is tapered such that a first end has a smaller diameter and a second end has a larger diameter.

15. A method of treating a pulmonary vein to electrically isolate arrhythmiatic foci, the method comprising:
    delivering, to an ostium of the pulmonary vein, a stent which carries at least one biologically active material; and
    deploying the stent in the pulmonary vein at a position to maintain patency of the pulmonary vein;
    wherein the biologically active material is delivered to tissue of the pulmonary vein engaged by the stent by iontophoresis; and
    wherein the biologically active material is an ablation causing agent.

16. The method of claim 15, wherein the stunt is positioned between the arrhythmiatic foci and a left atrium.

* * * * *